(12) United States Patent
Jolly et al.

(10) Patent No.: US 6,255,418 B1
(45) Date of Patent: Jul. 3, 2001

(54) CATALYSTS CONTAINING ORGANOCHROMIUM COMPOUNDS AND THEIR USE FOR POLYMERIZING ALKENES

(75) Inventors: Peter W. Jolly; Klaus Jonas, both of Mülheim an der Ruhr; Glenn P. J. Verhovnik, Geneva; Arno Döhring, Mülheim an der Ruhr; Jan Göhre, Düsseldorf; Jan Christoph Weber, Köln, all of (DE)

(73) Assignee: Studiengesellschaft Kohle mbH, Mulheim an der Ruhr (DE)

( * ) Notice: Subject to any disclaimer, the term of this patent is extended or adjusted under 35 U.S.C. 154(b) by 0 days.

(21) Appl. No.: 09/230,326

(22) PCT Filed: Jul. 18, 1997

(86) PCT No.: PCT/EP97/03868

§ 371 Date: Jan. 22, 1999

§ 102(e) Date: Jan. 22, 1999

(87) PCT Pub. No.: WO98/04570

PCT Pub. Date: Feb. 5, 1998

(30) Foreign Application Priority Data

Jul. 30, 1996 (DE) ............................................... 196 30 580
Mar. 14, 1997 (DE) ............................................... 197 10 615

(51) Int. Cl.$^7$ ....................................................... C08F 4/42
(52) U.S. Cl. ..................... 526/160; 526/104; 526/170; 526/154; 526/943; 526/348; 502/117; 502/152; 502/155
(58) Field of Search ..................................... 526/160, 170, 526/154, 943, 104, 348; 502/117, 152, 155

(56) References Cited

U.S. PATENT DOCUMENTS

| 4,015,059 | 3/1977 | Karol . |
| 5,418,200 | 5/1995 | Carney et al. . |

FOREIGN PATENT DOCUMENTS

| 4431838 | 3/1996 | (DE) . |
| 0416815 | 3/1991 | (EP) . |
| 0682037 | 11/1995 | (EP) . |
| 0 416 815 | * 5/1996 | (EP) . |
| 9411410 | 5/1994 | (WO) . |
| WO 96/13529 | * 5/1996 | (WO) . |

OTHER PUBLICATIONS

Organometallics, Band 16, Nr. 8, Apr. 1997, Rainer Emerich, et al., The Role of Metallacycles . . . Ethylene, pp. 1511–1513.

Organometallics, Band 15, 1996, Yuanfeng Liang et al., Constrained . . . Polymerization, pp. 5284–5286.

* cited by examiner

Primary Examiner—David W. Wu
Assistant Examiner—Ling-Siu Choi
(74) Attorney, Agent, or Firm—Norris McLaughlin & Marcus

(57) ABSTRACT

Novel donor ligand substituted $\eta^5$-organyl chromium complexes which, in admixture with Lewis acids, such as methylaluminoxane, form highly active polymerization catalysts for $\alpha$-alkenes and mixtures thereof and for mixtures of $\alpha$-alkenes and unsaturated alkenes with a strained double bond.

9 Claims, 2 Drawing Sheets

Molecular structure of $(Cy_2PC_2H_4C_5H_4)CrCl_2$ (VI)

Molecular structure of $(CH_2C_2H_4CH_2NC_2H_4C_5Me_4)CrMe_2$ (IX)

CATALYSTS CONTAINING ORGANOCHROMIUM COMPOUNDS AND THEIR USE FOR POLYMERIZING ALKENES

This application is a 371 of PCT/EP97/03868, which was filed on Jul. 18, 1997.

The present invention relates to a class of organochromium catalysts formed by a reaction of donor ligand substituted $\eta^5$-organyl chromium complexes with Lewis acids, which have a high catalytic activity in the polymerization and copolymerization of alkenes.

It is known that transition metal compounds with amido-substituted cyclopentadienyl ligands, above all with Ti (e.g., X) catalyze alkene polymerization in the presence of methylaluminoxane (MAO) [K. B. Sinclair and R. B. Wilson, Chem. Ind. 857 (1994); Dow Chemicals, Eur. Pat. 416 815 (1991); Exxon Chemicals, Eur. Pat. 420 436 (1991)], but corresponding systems with a donor ligand of group 15 (N, P, As, Sb, Bi) of the Periodic Table as a substituent have not been reported to date.

Surprisingly, it has now been found that organochromium compounds of general formula (I) can be employed in the polymerization and copolymerization of alkenes in the presence of Lewis acids, such as organyl compounds of boron or aluminum, e.g., methylaluminoxane:

I wherein $R^1$ contains a delocalized $\eta^5$-coordinated $\pi$ system, such as cyclopentadienyl, indenyl, fluorenyl;

X is an electronegative atom or group, such as halide or amide, or an organyl group, such as alkyl or aryl, or $CrX_2$ is a metallacyclic fragment, such as

Y is a donor atom of group 15 (N, P, As, Sb, Bi) of the Periodic Table;

Z is an atom of group 14 (C, Si, Ge, Sn, Pb) of the Periodic Table;

R' are H, organyl groups;

R" are H, organyl groups; and $n \geq 1$.

Typical Examples are compounds (II)–(IX); Table 1 defines the substituents $R^1$, R', R" and X, Y and Z (Cy represents cyclohexyl, Me represents methyl, and Et represents ethyl). The molecular structures of the novel compounds VI and IX were determined by X-ray crystallography and represented in FIGS. 1 and 2, respectively.

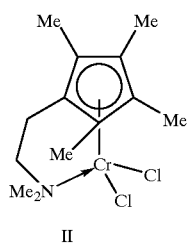

II

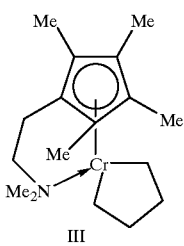

III

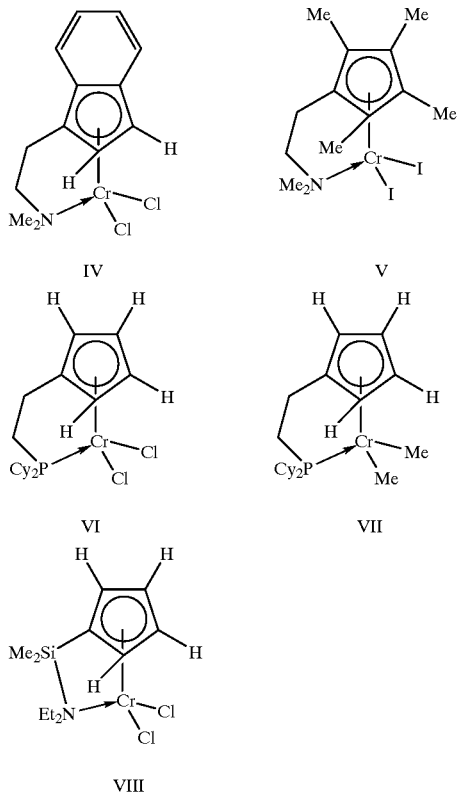

TABLE 1

Typical organochromium compounds

| Compound No. | X | Y | Z | n | $R^1$ | R' | R" |
|---|---|---|---|---|---|---|---|
| II | Cl | N | C | 2 | $C_5Me_4$ | H | Me |
| III | $C_2H_4^a$ | N | C | 2 | $C_5Me_4$ | H | Me |
| IV | Cl | N | C | 2 | indenyl | H | Me |
| V | I | N | C | 2 | $C_5Me_4$ | H | Me |
| VI | Cl | P | C | 2 | $C_5H_4$ | H | cyclohexyl |
| VII | Me | P | C | 2 | $C_5H_4$ | H | cyclohexyl |
| VIII | Cl | N | Si | 1 | $C_5H_4$ | Me | Et |
| IX | Me | N | C | 2 | $C_5Me_4$ | H | $C_2H_4^b$ |

$^a \overline{CrCH_2C_2H_4CH_2} = CrX_2$

$^b \overline{NCH_2C_2H_4CH_2} = YR_2''$

The organochromium compounds are obtained in high yields by the reaction of a Cr trihalide with a metal salt of the corresponding donor ligand substituted $\eta^5$-organyl derivative, e.g.:

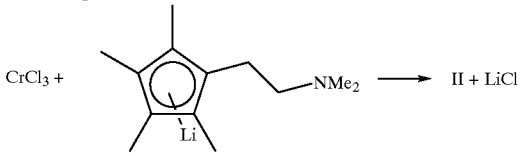

wherein the resulting Cr dihalide derivatives can be used as the starting compounds for the preparation of further examples, e.g.:

VI+2LiMe→VII+2LiCl

Activating those compounds with Lewis Acids results in highly active catalysts for alkene polymerization and copolymerization. Preferred alkenes are α-alkenes, while ethene is preferred in the copolymerization with strained alkenes. Examples 9–15 deal with ethene, Examples 16 and 17 with propene, and Example 18 with copolymerization. The reaction may be performed in aromatic solvents (toluene) or saturated hydrocarbons (n-heptane), at room temperature (20–30° C.) and low pressures (2 bar). Surprisingly, the full catalytic activity is achieved with an Al:Cr molar ratio of 45–300:1 already. In contrast, the Ti based system X and the Zr containing ansa-metallocenes, e.g., XI [M. Aulbach and F. Küber, Chem. unser. Zeit 28, 197 (1994)], required Al:metal ratios of about $10^4$:1.

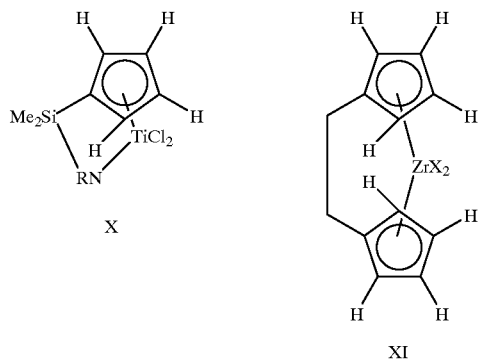

In the presence of MAO, the novel Cr compounds, preferably compounds VII and IX, catalyze the polymerization of ethene to give highly linear polyethylene having a bimodal molecular weight distribution (Table 3). In addition, homologous alkenes, such as propene, can also be polymerized (atactic polypropylene), and ethene, for example, can be copolymerized with norbornene. In the latter case, an almost purely alternating copolymer (XII) is generated which contains 43% of norbornene and 57% of ethene as determined by $^{13}$C NMR, and exclusively has exo configurations at the bicyclic ring.

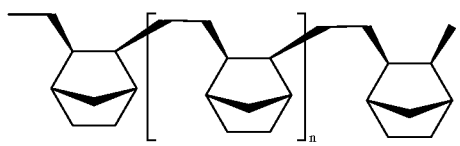

BRIEF DESCRIPTION OF THE DRAWINGS

FIG. 2 is the molecular structure of

(IX)

$(CH_2C_2H_4CH_2NC_2H_4C_5Me_4)CrMe_2$

EXAMPLES

Example 1

Preparation of $(Me_2NC_2H_4C_5Me_4)CrCl_2$ (II)

Figure 1:
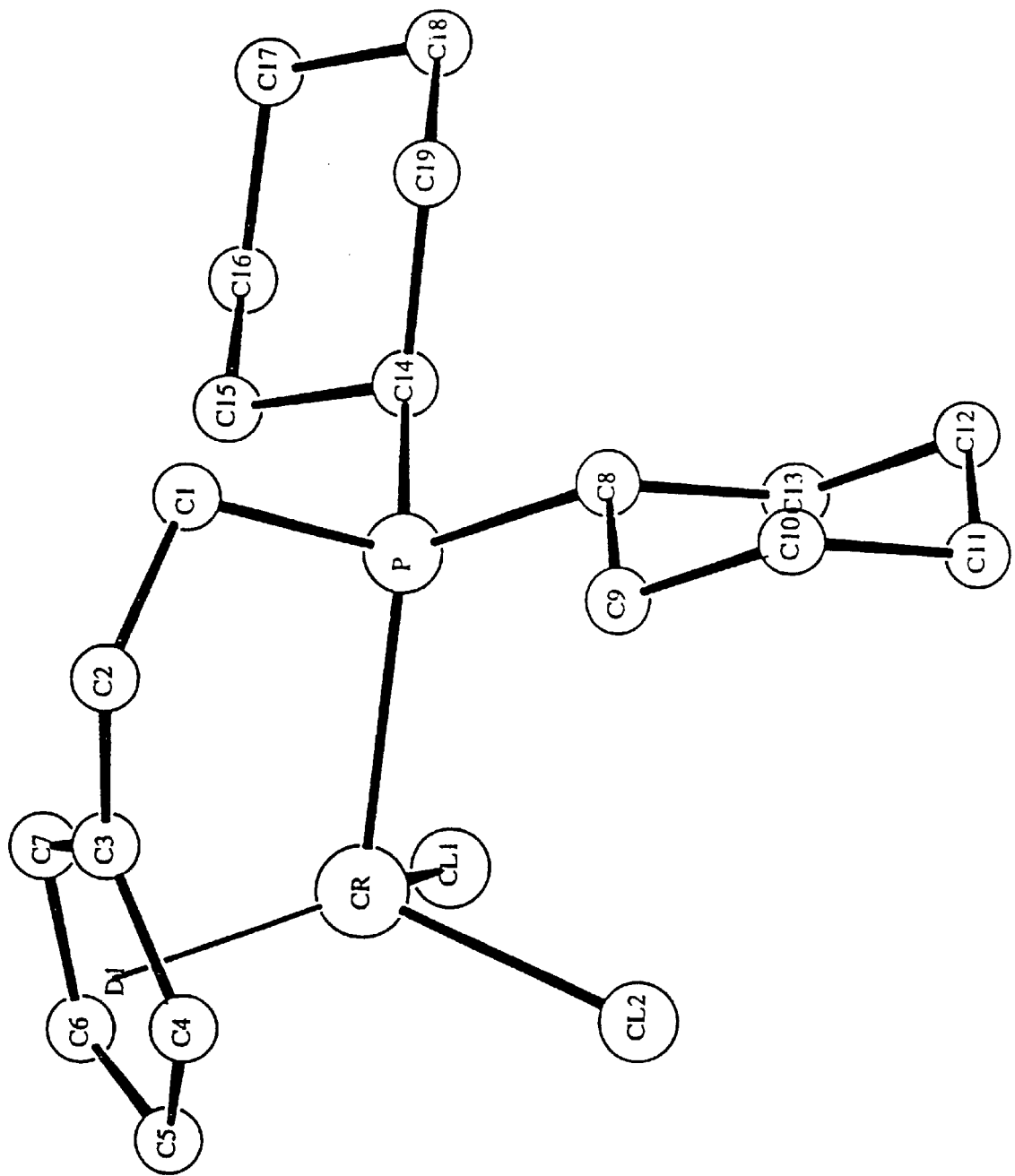
FIG. 1 is the molecular structure of $(Cy_2PC_2H_4C_5H_4)CrCl_2$ (VI).

$Me_2NC_2H_4C_5Me_4Li$ (1.25 g, 6.3 mmol) in THF (20 ml) was added dropwise with stirring to a solution of $Cr(THF)_3Cl_3$ (2.36 g, 6.3 mmol) in THF (50 ml) at room temperature. The resulting blue solution was stirred for another 15 h and then concentrated to dryness in vacuo. The residue was extracted with boiling toluene. The product precipitated from the extract at −70° C. in the form of dark-blue needles. Yield: 1.70 g (86% of theory). Analytical data: calc. for $C_{13}H_{22}Cl_2CrN$: C 49.5, H 7.0, Cr 16.5, Cl 22.5, N 4.4%; found C 49.5, H 6.9, Cr 16.5, Cl 22.6, N 4.4%. MS (100° C.): m/e 314 (6%, M⁺), 278 (10%).

Example 2

Preparation of (III)

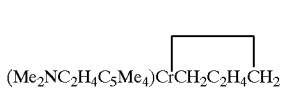

$(Me_2NC_2H_4C_5Me_4)CrCH_2C_2H_4CH_2$

To a solution of IV (1.43 g, 4.5 mmol) in THF (50 ml) was added 1,4-dilithiumbutane dissolved in diethyl ether (16.0 ml of an 0.32 M solution, 5.1 mmol), diluted with THF (20 ml), at −20° C. The reaction mixture was stirred at −10° C. for 15 h, and the resulting green solution was concentrated to dryness in vacuo. The residue was extracted with pentane at 0° C. From the extract whose volume had been reduced to 20 ml, the product precipitated at −70° C. in the form of dark-green needles. Yield: 1.04 g (77% of theory). The compound is stable at room temperature. Analytical data: calc. for $C_{17}H_{30}CrN$: C 68.0, H 10.1, Cr 17.3, N 4.7%; found C 67.9, H 10.0, Cr 17.4, N 4.6%. MS (50° C.): m/e 272 (21%, M⁺−$C_2H_4$), 244 (100%).

Example 3

Preparation of $(1-Me_2NC_2H_4indenyl)CrCl_2$ (IV)

$1-Me_2NC_2H_4$-indenyl-K (3.88 g, 17.2 mmol) in THF (50 ml) was added dropwise with stirring to a solution of $Cr(THF)_3Cl_3$ (6.45 g, 17.1 mmol) in THF (100 ml) at room temperature. The resulting green-blue solution was stirred for another 17 h and then concentrated to dryness in vacuo. The residue was extracted with boiling toluene. The product precipitated from the extract at −70° C. in the form of dark-green needles. Yield: 3.86 g (73% of theory). Analytical data: calc. for $C_{13}H_{16}Cl_2CrN$: C 50.5, H 5.3, Cr 16.8, Cl 22.9, N 4.5%; found C 50.6, H 5.3, Cr 16.7, Cl 22.9, N 4.5%. MS (100° C.): m/e 308 (10%, M⁺), 122 (9%).

Example 4

Preparation of $(Me_2NC_2H_4C_5Me_4)CrI_2$ (V)

$(Me_2NC_2H_4C_5Me_4)CrCl_2$ (II, 1.23 g, 3.9 mmol) in THF (100 ml) was stirred with KI (3.1 g, 18.7 mmol) at 45° C. for 72 h. The solution was concentrated, and the resulting compound was recrystallized from heptane/toluene (1:9). The product precipitated from the extract in the form of light-blue needles. Yield: 1.52 g (83% of theory). Analytical data: calc. for $C_{13}H_{22}CrI_2N$: C 31.4, H 4.5, Cr 10.9, I 51.0, N 2.8%; found C 30.9, H 4.8, Cr 11.6, I 49.1, N 3.2%. MS (100° C.): m/e 498 ($M^+$), 371 ($M^+$−1).

Example 5

Preparation of $(Cy_2PC_2H_4C_5H_4)CrCl_2$ (VI)

To a solution of $Cr(THF)_3Cl_3$ (2.6 g, 6.7 mmol) in THF (50 ml) was added $LiPCy_2C_2H_4C_5H_4$ (2.8 g, 6.7 mmol) in THF (20 ml) at room temperature, and the solution was stirred for 5 min. The resulting blue solution was concentrated, and the residue was recrystallized from boiling acetone. Yield: blue needles, 82% of theory. Analytical data: calc. C 55.4, H 7.3, Cl 17.2, Cr 12.6, P 7.5; found C 55.2, H 7.3, Cl 17.1, Cr 12.7, N 7.7%. Crystal structure: FIG. 1.

Example 6

Preparation of $(Cy_2PC_2H_4C_5H_4)CrMe_2$ (VII)

To a solution of $(Cy_2PC_2H_4C_5H_4)CrCl_2$ (VI, 1.1 g, 2.6 mmol) in THF (50 ml) was added dropwise methyl lithium (5.2 mmol in diethyl ether), diluted in THF (20 ml), at −20° C. within 2 h. The reaction mixture was then stirred at −10° C. for 15 h upon which the solution turned from violet to dark-green. After removing all volatile components at −10° C., the residue was extracted with pentane at −30° C. The compound precipitated from the extract at −30° C. in the form of dark-green needles. Yield: 40% of theory. Analytical data: MS (EI, 70 eV): 371 ($M^+$), 338.

Example 7

Preparation of $(Et_2NSiMe_2C_5H_4)CrCl_2$ (VIII)

A solution of $LiEt_2NSiMe_2C_5H_4$ (3.5 g, 17.2 mmol) in toluene (50 ml) was added to a suspension of $Cr(THF)_3Cl_3$ (6.6 g, 17.5 mmol) in THF (100 ml) at 20° C. to give a deep-blue solution. After stirring for 2 h, the solvent was distilled off, and the oily residue was extracted with pentane (200 ml). The compound precipitated in the form of black crystals. Yield: 3.1 g (56% of theory). Analytical data: Crystal structure; the compound is dimeric in nature.

Example 8

Preparation of (IX)

$(CH_2C_2H_4CH_2NC_2H_4C_5Me_4)CrMe_2$

To a suspension of $Cr(THF)_3Cl_3$ (4.61 g, 12.3 mmol) in THF (100 ml) was added a solution of

Figure 2:
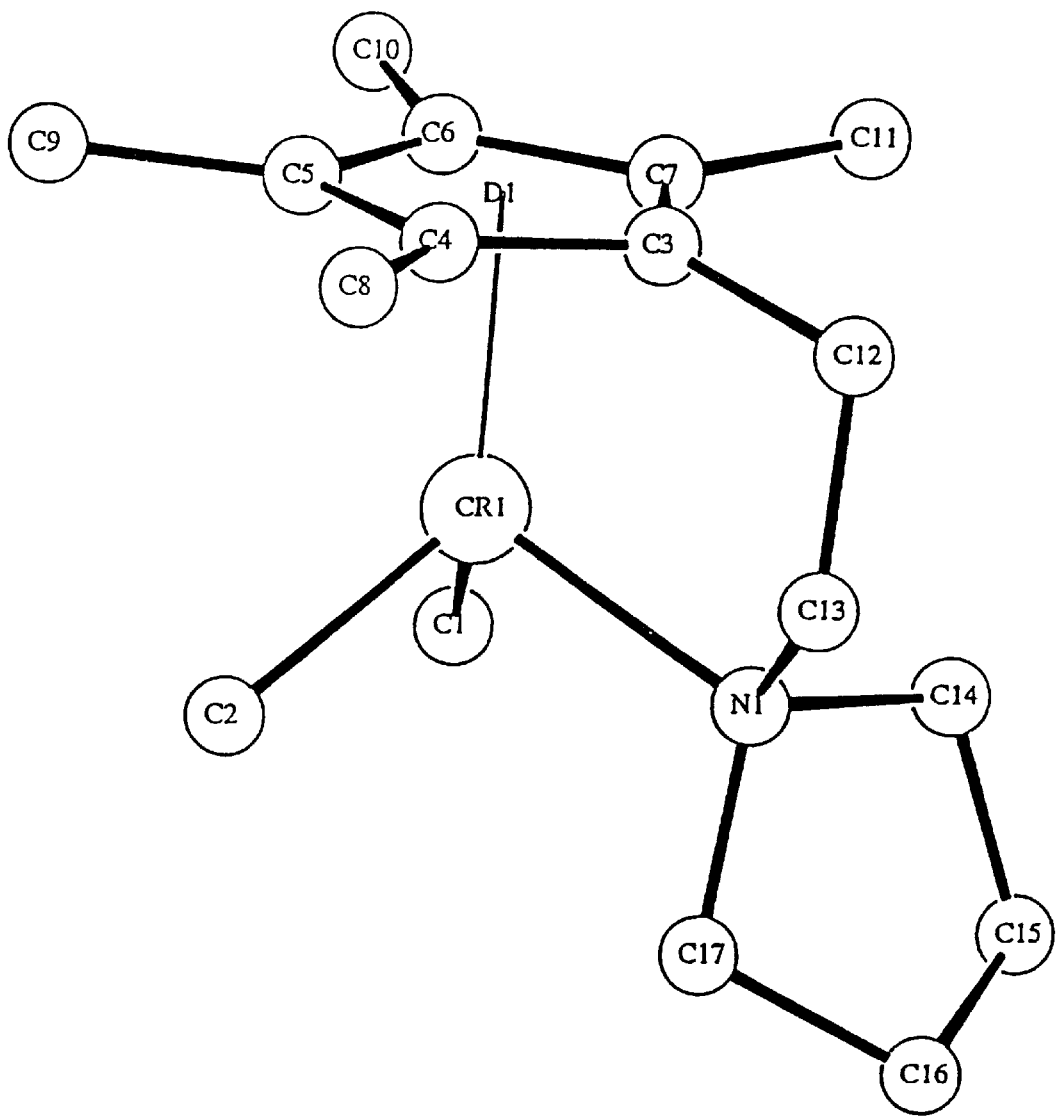

$CH_2C_2H_4CH_2NC_2H_4C_5Me_4Li$ (2.69 g, 12.0 mmol) in THF (100 ml) dropwise at room temperature. The deep-blue solution was stirred for 2 h, cooled to −20° C., and MeMgCl (9.4 ml of a 2.815 M solution in THF; 26.3 mmol) in THF (10 ml) was added dropwise within 10 min. The dark-green solution was stirred at room temperature for 1 h, concentrated in vacuo, and the residue was extracted with pentane (200 ml). Cooling to −70° C. yielded the compound in the form of dark-green cubic crystals. Yield: 3.09 g (86% of theory). Analytical data: calc. for $C_{17}H_{30}CrN$: C 68.0, H 10.1, Cr 17.3, N 4.7%; found C 68.1, H 10.1, Cr 17.3, N 4.6%. MS (100° C.): m/e 301 (4%, $M^+$+H), 285 (23%), 199, 186. Crystal structure: see FIG. 2.

Catalytic Alkene Polymerization

In the following, examples of the polymerization of ethene (9–15), propene (16, 17), and of the copolymerization of ethene with norbornene (18) are given. For experiments 9–11 and 13–15, a glass autoclave equipped with a glass blade stirrer was used at a stirring speed of 1200 rpm. Experiment 12 was performed at about 50 bar in a steel autoclave which also had a blade stirrer. For experiments 16–18, a simple steel autoclave with a magnetic stirring bar was employed.

Ethene Polymerization

Examples 9–15.

The reaction conditions are summarized in Table 2, and the physical properties of the polyethylene obtained are given in Table 3. Remarkable features are the high activity of the Cr catalysts, the low MAO:Cr ratio, and the high linearity of the polyethylene.

Propene Polymerization

Example 16

Catalyst, $(Me_2NC_2H_4C_5Me_4)CrCl_2$ (II), 0.0033 mmol; cocatalyst, MAO; Al:Cr, 100:1; solvent, toluene; temp., 23/33° C.; t, 60 min; p, 9 bar; polymer, 2.91 g; TON/h, 20,996; catalytic activity [kg of PP/mol of Cr.h], 882.

Example 17

Catalyst, $(Me_2NC_2H_4C_5Me_4)CrCl_2$ (II), 0.0031 mmol; cocatalyst, MAO; Al:Cr, 100:1; solvent, n-heptane; temp., 23/35° C.; t, 60 min; p, 9 bar; polymer, 4.53 g; TON/h, 34,793; catalytic activity [kg of PP/mol of Cr.h], 1461.

In both cases, a viscous polymer results which is completely soluble in diethyl ether and chloroform. The $^{13}C$ NMR spectrum confirms the atactic conformation of the polypropylene.

Example 18

Copolymerization of Ethene with Norbornene

Catalyst, (III)

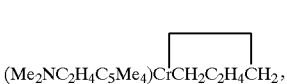
$(Me_2NC_2H_4C_5Me_4)CrCH_2C_2H_4CH_2$, 0.0017 mmol; cocatalyst, MAO; Al:Cr, 2000:1; temp., 40–80° C.; t, 12 min; p, 21 bar ($C_2H_4$); polymer, 44.6 g; catalytic activity [kg of polymer/mol of Cr.h], 131,177. From the signal intensities in the $^{13}C$ NMR spectrum (1,2,4-trichlorobenzene/$CHD_2CHD_2$, 395 K), it can be seen that an alternating polymer was formed which contained 43% of norbornene and 57% of ethene. Glass transition temperature: 131° C.

TABLE 2

| | | | Cr-catalyzed ethene polymerization | | | | |
|---|---|---|---|---|---|---|---|
| Examples | 9 | 10 | 11 | 12 | 13 | 14 | 15 |
| Cr compound | II | III | IV | V | VII | VIII | IX |
| temp. (° C.) | 25–33 | 25–41 | 28–42 | 19–67 | 27–69 | 26–29 | 26.4–57.3 |
| p (bar) | 2 | 2 | 2 | 50–44 | 2 | 2 | 2 |
| t (min) | 18 | 7 | 13 | 60 | 7 | 47 | 5.5 |
| polyethylene (g) | 5.2 | 5.8 | 18.8 | 4.4 | 25.6 | 12.2 | 13.8 |
| TON/h | 206,349 | 538,033 | 416,552 | 43,221 | 700,037 | 11,678 | 1,536,419 |
| activity (kg of PE/mol [Cr] · h) | 5778 | 15,065 | 11,718 | 1212 | 19,763 | 328 | 44,118 |

TABLE 3

| | Physical properties of the polyethylene formed | | | | |
|---|---|---|---|---|---|
| Example | cryst. (%) | $T_m$ (° C.) | structure | $M_w$ | $M_w/M_n$ |
| 9 | 71 | 127 | linear | $2.9 \times 10^5$ | 5.0 |
| 10 | 66 | 126 | linear | $2.2 \times 10^5$ | 3.9 |
| 11 | 74 | — | linear | — | — |

Comparative Experiment

For comparing the catalytic activities, a comparative experiment was performed with a Ti(III) compound of the DSM application EP-A-0 789 718=WO 96/13529. It proves that this Ti compound is hardly active under the same mild conditions as used with the chromium catalyst of the present application WO 98/04570: 13 kg of polymer/mol of titanium per hour as compared to $44 \times 10^3$ kg of polymer/mol of chromium per hour.

Example A: Comparison with the catalyst from EP-A-0 789 718:

Catalyst, $(C_4H_8NC_2H_4C_5Me_4)TiCl_2$, 0.0572 mmol; cocatalyst, MAO; Al:Ti, 104:1; solvent, toluene; temp., 20.7° C.; t, 26 min; p, 2.05 bar; polymer, 0.31 g; catalytic activity (kg of polymer/mol of Ti.h), 13.

Under similar conditions, the analogous Cr compound—$(C_4H_8NC_2H_4C_5Me_4)CrCl_2$/MAO (see above, Example 15 of the present application)—has a catalytic activity (kg of polymer/mol of Cr.h) of $44 \times 10^3$!

What is claimed is:

1. A polymerization catalyst, containing at least one organochromium compound of general formula I:

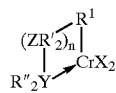

I wherein $R^1$ contains a delocalized $\eta^5$-coordinated $\pi$ system;

X is an electronegative atom, halogen, amide, or organyl group, or $CrX_2$ is a metallacyclic fragment;

Y is a donor atom of group 15 (N, P, As, Sb, Bi) of the Periodic Table;

Z is an atom of group 14 (C, Si, Ge, Sn, Pb) of the Periodic Table;

R' are H, organyl groups;

R" are H, organyl groups; and $n \geq 1$.

2. The polymerization catalyst according to claim 1, wherein said organochromium compounds are mixed with Lewis acids.

3. The polymerization catalyst according to claim 2, wherein said Lewis acid is methylaluminoxane.

4. The polymerization catalyst according to claim 1, wherein the Al:Cr molar ratio in the catalyst is from 40 to 500.

5. The polymerization catalyst according to claim 1, wherein said delocalized $\eta^5$-coordinated $\pi$ system is cyclopentadienyl or indenyl.

6. The polymerization catalyst according to claim 1, wherein $R^1 = \eta^5$—$C_5H_4$, X=$CH_3$, Y=P, and Z=C.

7. A process for the polymerization of α-alkenes by allowing a polymerization catalyst according to one of claims 1 to 6 to act on α-alkenes.

8. A process for the copolymerization of alkenes by allowing a polymerization catalyst according to one of claims 1 to 6 to act on a mixture of alkenes and unsaturated alkenes with a strained double bond.

9. The process according to claim 8, wherein the polymerization catalyst is allowed to act on a mixture of ethylene and an alkene with a strained double bond.

* * * * *

UNITED STATES PATENT AND TRADEMARK OFFICE
CERTIFICATE OF CORRECTION

PATENT NO.     : 6,255,418 B1
DATED          : July 3, 2001
INVENTOR(S)    : Peter W. Jolly et al.

It is certified that error appears in the above-identified patent and that said Letters Patent is hereby corrected as shown below:

<u>Column 8,</u>
Lines 45 and 48, change "by allowing a polymerization" to -- by allowing at least one polymerization --

Signed and Sealed this

Sixteenth Day of September, 2003

JAMES E. ROGAN
*Director of the United States Patent and Trademark Office*